United States Patent [19]

Wiesner et al.

[11] 4,331,802
[45] May 25, 1982

[54] ORGANOMETALLIC REAGENTS AND THEIR USE IN THE SYNTHESIS OF CARDENOLIDES AND ISOCARDENOLIDES

[75] Inventors: Karel Wiesner; Rinaldo Marini-Bettolo; Connie S. J. Tsai; Thomas Y. R. Tsai, all of Fredericton, Canada

[73] Assignee: Advance Biofactures Corporation, Lynbrook, N.Y.

[21] Appl. No.: 193,175

[22] Filed: Oct. 1, 1980

[51] Int. Cl.³ .............................................. C07J 7/00
[52] U.S. Cl. .................................. 536/5; 260/239.57; 260/239.55 R; 549/214; 549/479
[58] Field of Search ........................... 536/5; 260/347.8

[56] References Cited

U.S. PATENT DOCUMENTS 4,242,332 12/1980 Albrecht et al. ........................ 536/5

Primary Examiner—Elbert L. Roberts
Attorney, Agent, or Firm—Roland Plottel

[57] ABSTRACT

A method for synthesizing a cardenolide or isocardenolide by subjecting an $\alpha,\beta$-unsaturated steroidal 17-ketone to a double bond shift and hydrogenation to produce a (C/D cisoid) ketone which is treated with an organometallic reagent to yield a tertiary alcohol and the acidifying said alcohol to produce said cardenolide or isocardenolide is shown. The invention also relates to organometallic reagents particularly useful in such method.

6 Claims, 1 Drawing Figure

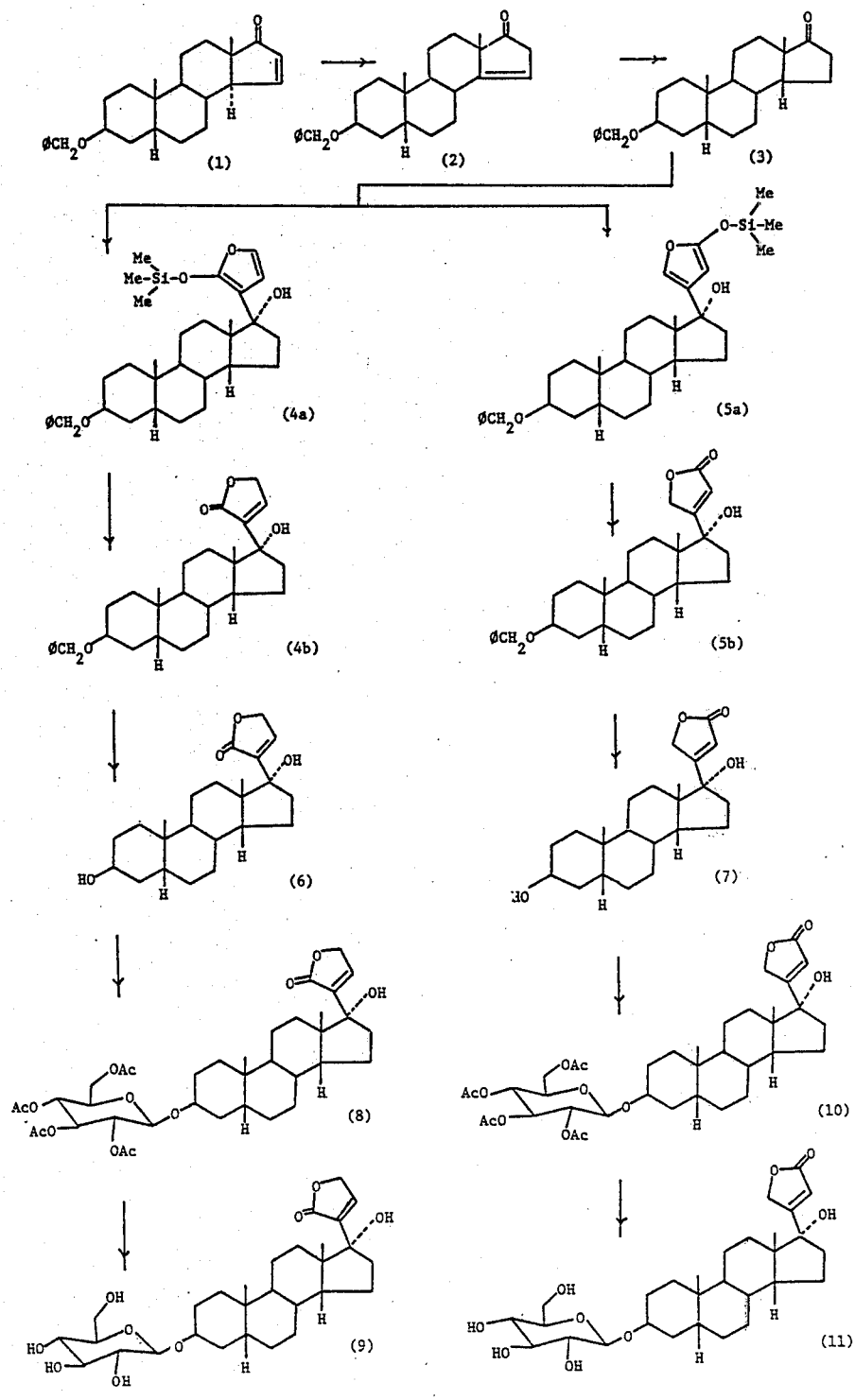

ORGANOMETALLIC REAGENTS AND THEIR USE IN THE SYNTHESIS OF CARDENOLIDES AND ISOCARDENOLIDES

CROSS REFERENCE TO RELATED APPLICATION

Reference is made to the corresponding U.S. application Ser. No. 080,004 of Karel Wiesner, et al, filed Sept. 28, 1979 for Synthesis of Furyl Intermediates and Cardenolides and Their Isomers Prepared Therefrom.

This invention relates to the preparation of certain organometallic reagents, and the use of such reagents in the synthesis of cardenolides and isocardenolides.

BACKGROUND OF THE INVENTION

Cardenolides are compounds that can be and are used to treat people suffering from various heart diseases. These materials include digitalis which is a mixture of glycosides and affords on hydrolysis a mixture of the aglycones, for example, digitoxigenin, digoxigenin, gitoxigenin, and many others which are also cardenolides. These substances conform in skeletal structure; with the exception of the placement of hydroxyl groups they all have twenty-three carbon atoms present and are of the cis- decalin type. They are all sterols and are characterized structurally by the presence of a saturated phenanthrene ring system having an additional five membered ring fused thereto. The distinguishing structural features of the cardenolides are the $\beta$-oriented hydroxyl group at $C_{14}$ and as stated the five-membered $\alpha\beta$-unsaturated lactone ring. As indicated above, the compounds are of the cis-decalin type, the angular methyl group and side chain are $\beta$-oriented, the B/C ring structure is trans while the C/D structure is cis since $C_{14}$ has the $\beta$ configuration. This is structurally shown in Formula 1.

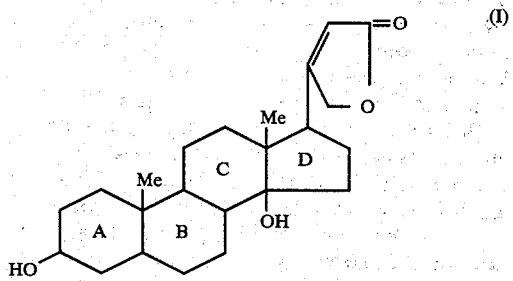

which represents digitoxigenin. Digoxigenin and gitoxigenin have an additional hydroxyl group on the 12-carbon and 16-carbon respectively.

Furyl derivatives of cardenolides have been heretofore obtained by hydride reduction of naturally occurring cardenolides. These derivates obtained from naturally occurring cardenolides have the structure shown in Formula II.

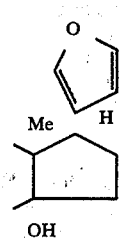

Oxidation of these furyl derivatives with peracids or N bromo succinimide respectively yielded selectively lactones of the types III and IV.

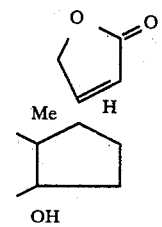

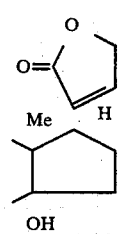

(J. M. Ferland, Y. Lefebre, R. Deghenghi and K. Wiesner, Tetrahedron Letters, No. 30, 3617 (1966).)

In the above identified U.S. application Ser. No. 080,004 (which is incorporated herein by reference), we have shown that natural cardenolides and cardenolides analogues may be synthesized by a method which features the reaction of an appropriate steriodal ketone with $\beta$-furyl lithium and an oxidative and reductive conversion of the furan ring into a five-membered unsaturated lactone.

SUMMARY OF THE INVENTION

It is the primary object of the subject invention to provide certain organometallic reagents useful in the subsequent production of synthetic cardenolides and their isomers.

A second object of the instant invention is to use said organometallic reagents to produce said synthetic cardenolides and their isomers.

Still other objects will become apparent from the ensuing description and claims.

We have discovered an improved method of converting the corresponding steroid furan derivative into an $\alpha,\beta$-unsaturated lactone. For this purpose we have developed new organometallic reagents of the following type represented by formulas V and VI:

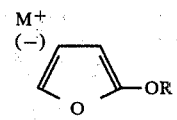

-continued

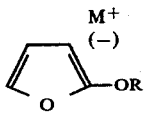
VI

The R group in these reagents may be any readily removable blocking group. Thus the group defined by R could be alkyl, trialkylsilyl, alkoxy alkylene, aralkyl, alkoxy aralkyl, tertiary alkyl, and others. The alkyl, alkoxy or alkylene groups should contain from one to four carbon atoms ($C_1$–$C_4$). Specifically the R groups can include trimethylsilyl (—Si(Me)(Me)(Me)), methyl (—Me), methoxy

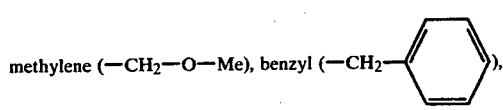

methylene (—CH₂—O—Me), benzyl (—CH₂—Ph),

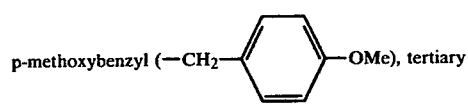

p-methoxybenzyl (—CH₂—C₆H₄—OMe), tertiary butyl (—C(Me)(Me)(Me))

and others. The reagents V and VI are prepared by treatment with an organometallic compound, for instance n-butyl lithium, of the corresponding halogen derivatives, for example, the bromocompounds VII and VIII below:

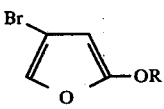
VII

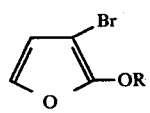
VIII

Reaction of appropriately constituted steroidal 17-ketones with the reagents V and VI yields tertiary alcohols which can be protrayed by the general formulae IX and X below. These alcohols are converted into cardenolides either spontaneously on treatment with water (R = —Si(Me)(Me)(Me)), by hydrogenolysis

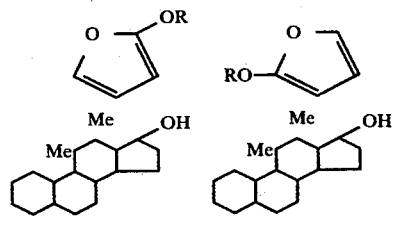

IX            X (R = —CH₂—C₆H₅), by acid treatment (R = —C(Me)(Me)(Me), —CH₂—O—Me, —CH₂—C₆H₄—OMe)

or an acidic ion exchange resin (R=Me).

The conversion of the tertiary alcohols of the type IX and X into cardenolides may be performed either before or after a further modification of the functional group system.

DESCRIPTION OF THE DRAWING

The single FIGURE represents the steps of a synthesis in accordance with the invention of the instant case.

DETAILED DESCRIPTION OF THE INVENTION

The 17-steroidal ketones are known in the art and can be readily prepared from testosterone or other well known steroids (McQuillen et. al., Journal of Chemical Society, pg. 5996 (1963); Danielsson et. al., Journal Biog. Chem. 237, 3657 (1962); Kelly et. al., Journal Chemical Society, pg. 416 (1969)).

The following description illustrates an 11 step manner of preparation of the steroidal ketone useful in the preparation of the furyl intermediates:

(1) Commercial testosterone (25 g.) was dissolved in ethanol (400 ml.) and dioxane (100 ml.). Potassium hydroxide solution (1.5 g in 20 ml. of water) was added to bring the pH of the solution to 10.5. 10% Palladium on calcium carbonate (3 g.) was added and the suspension was hydrogenated at atmospheric pressure until there was no more uptake of hydrogen. The catalyst was filtered off through a Celite pad and the solvent was evaporated in vacuo to give a yellowish gum. The product alcohol crystallized out on addition of ice water, and was recrystallized from acetone-hexane. The yield was 24.1 g. (96.4%, m.p. 137°–140° C.).

(2) The alcohol (24 g., 82 mol) was dissolved in dry methylene chloride (500 ml.). Dihydropyran (14 g.) was added followed by pyridinium p-toluene-sulphonate (2.5 g.). After 4 hours the solution was evaporated to a small volume and then diluted with ether (IL). The ether solution was washed with brine, dried over magnesium sulfate and evaporated to afford the product ketone as a gum which crystallized on trituration with hexane at 0° C. (30.1 g., 96.3%, m.p. 83°–5° C.).

(3) The ketone thus formed (30 g.) was dissolved in absolute benzene (150 ml.) and sec-butyl alcohol (450 ml.) was added. Aluminum t-butylate (80% in t-butyl alcohol, 35 g.) was then added and the suspension was heated under reflux for 15 minutes. The reaction mixture was then added to ice-water and the resulting solid extracted with 1:3 methylene chloride-ether (3×500 ml.). The combined organic extracts were washed with saturated ammonium chloride and brine, dried over sodium sulfate, and evaporated to afford the mixture of compounds 4a and 4b. The mixture was separated by short-column chromatography with ether-hexane 3:7 as solvent to give compounds one having a melting point of 148°–150° C. and another having a melting point of 129°–130° C., in a total yield of 94.5%.

(4) 19 grams of the second compound in dry methylene chloride was added while vigorously stirring to a suspension of chromium trioxide pyridine complex. Stirring was continued until the reaction was completed (20 min.) The solvent was decanted and the complex washed with more methylene chloride (2×200 ml.). The solvent was then reduced to a small volume in vacuo and diluted with ether (800 ml.). The ethereal layer was washed with saturated sodium bicarbonate, followed by brine. The total organic extract was dried over magnesium sulfate and evaporated to yield the ketone from the previous step as a gum (18 g.). This material was used directly without purification and reduced to the mixture of the two compounds above.

(5) The first compound (103 g.) was dissolved in dry dioxane (50 ml.) and sodium hydride (360 mg., 57% dispersion in oil) was added under an atmosphere of nitrogen. The suspension was heated with stirring under reflux for 4 hours and then allowed to cool. Benzyl bromide (560 mg.) was added and refluxing was continued for a further 2 hours. The suspension was filtered through a sintered glass funnel and the filtrate was evaporated in vacuo to give the product as a gum. This material was used directly for the next reaction without purification (1.1 g.).

(6) The crude product from (5) above (1.1 g.) was dissolved in 2% hydrochloric acid in methanol (150 mg.) and stirred 1 hour. The solution was neutralized with 10% sodium hydroxide and the volume of methanol reduced in vacuo. The aqueous residue was then extracted with 1:3 methylene chloride-ether (3×100 ml.). The combined organic extracts were washed with brine, dried over sodium sulfate and evaporated to afford a product alcohol as a form (900 mg.).

(7) The alcohol (13 g.) was dissolved in dry methylene chloride (200 ml.) and added to a rapidly stirring suspension of the chromium trioxide pyridine complex (50 g.) in dry methylene chloride (800 ml.) at room temperature. Stirring was continued for a further 20 minutes and the solvent decanted and evaporated in vacuo to a small volume. Ether (600 ml.) was added and the organic layer washed with saturated sodium bicarbonate followed by brine. Drying, evaporation of the solvent and crystallization from ethanol yielded a ketone (11.3 g., 87.9%, m.p. 134°–6° C.).

(8) The ketone (11 g.) was dissolved in absolute benzene (350 ml.) and ethylene glycol (25 ml.) and p-toluenesulphonic acid (1.1 g.) were added. The solution was heated, with stirring, under reflux for 5 hours and water was collected by means of a Dean-Stark apparatus. The solution was then allowed to cool and it was diluted with more benzene (50 ml.), and washed with saturated sodium bicarbonate, followed by brine. Drying, evaporation of the benzene and crystallization from ether-hexane gave the product, m.p. 95°–7° C. (97%).

(9) The acetal (12 g.) thus formed was dissolved in freshly distilled tetrahydroguran (30 ml.). Pyridinium bromide perbromide (10 g.) was dissolved in dry tetrahydrofuran (30 ml.) and added to the solution under a nitrogen atmosphere. The solution was stirred for 1 hour after which time there was precipitation and lightening of the color of the reaction mixture. Sodium iodide (7.5 g.) was added to the suspension and stirring was continued for a further 15 minutes. The solution was then diluted with ether and washed with saturated sodium thiosulfate followed by brine. Drying and evaporqtion yielded a product bromoacetal as a gum which was crystallized from aqueous methanol (11.5 g., 80.9%, m.p. 109°–111° C.).

(10) The bromoacetal (11.5 g., 23 mmol) was partially dissolved in dimethylsulfoxide (150 ml.) and potassium t-butoxide (12 g., 98 mmol) was added under a nitrogen atmosphere. The suspension was stirred at 40° C. for 12 hours and the resulting solution was poured into dry ether (1 liter). The ether was then washed with water, followed by brine. The ether solution was dried over magnesium sulfate and evaporated to dryness to afford the product acetal as a foam (8.8 g., 90%).

(11) This acetal (8.8 g.) was dissolved in acetone (300 ml.) and p-toluenesulphonic acid (1 g.) was added followed by water (40 ml.). The solution was stirred for 3 hours at room temperature and diluted with 3:1 ether-methylene chloride (1 liter). The solution was then washed with saturated sodium bicarbonate and by brine. Drying and evaporation of the solvent affroded the steroidal ketone as a white solid which was recrystallized from ether-hexane (m.p. 151°–3° C., 7.5 g., 95%).

Thus, the product useful as the starting material for the synthesis of cardenolides and isocardenolides is an α,β-unsaturated ketone having steroidal properties.

Referring now to the FIGURE, the α,β-unsaturated ketone is designated therein as (1). The α,β-unsaturated ketone (1) is converted to a compound (3) by an acid catalyzed double bond shift followed by hydrogenation. The (C/D cisoid) ketone (3) is now treated with the organometallic reagent, formula VI above ($M^+ = Li^+$, $R = Si(CH_3)_3$) and yields the labile tertiary alcohol (4a) which is shown in brackets in the FIGURE because it cannot be isolated as a stable characterizable intermediate.

The material, without isolation, gives the crystalline isocardenolide (4b) spontaneously on mild acidic work up. Hydrogenolysis of (4b) yields the alcohol (6). Conversion of compound (6) to a β-glucoside, the glucosidation with acetobromoglucose (tetra-O-acetyl-α-D-glucopyranosyl bromide) and silver oxide yields the glucoside acetate (8), which is subsequently hydrolyzed to the glucoside, yields compound (9), and artificial synthetic analogue of natural cardiotonic glycosides with a modified lactone attachment.

In exactly the same manner substituting the organometallic reagent (formula V above) ($M^+ = Li^+$, $R = Si(CH_3)_3$) for the reagent VI, the compounds 5a, 5b, 7, 10 and 11 were prepared. (Similar to 4a above, compound 5a is indicated in brackets in the Figure because it cannot be isolated as a stable, characterizable intermediate.) The compound (11) is an artificial synthetic analogue of natural cardiotonic glycosides with a normal lactone attachment. Preliminary pharmacological testing of compound (11) revealed an inotropic effect weaker than in natural cardiotonic glycosides. On the other hand, compound (11) seemed to display a greater margin of safety and reversibility of toxic effects than manifested by the natural digitalis glycosides currently used in therapy.

The R groups which can be used in principle are those previously indicated, i.e., any readily removable blocking group. These include trimethylsilyl, methyl, methoxymethylene, benzyl, p-methoxybenzyl, tertiary butyl, and others. The cleavage of the R group and conversion to cardenolides occurs in steroid furan derivatives, when R is a tertiary butyl group with dilute aqueous acid (HCl, $H_2SO_4$), when R is a methyl group, by an acidic ion exchange resin.

The $M^+$ is preferably lithium ion because of the advantageous reaction of the substituted bromo-furans with the readily available n-butyl lithium. Postassium, sodium and magnesium may also be employed. Potassium and sodium derivatives would be prepared in an analogous manner to the lithium derivatives. Magnesium derivatives can be prepared by reaction of the substituted bromofurans with metallic magnesium, for example

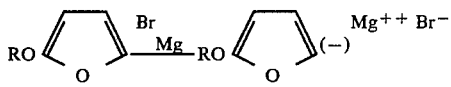

A more detailed analysis of the organometallic reagents and the synthesis of the cardenolides and isocardenolides is given in the following Examples:

EXAMPLE I

Preparation of 3-bromo-2-trimethylsilyloxyfuran (formula VIII above) [R=—Si(CH$_3$)$_3$]

The known α-bromo-crotonolactone (m.p. 58°, Beil. 17, Erg. III/IV 4295) in dry THF was stirred for 12 hours at 65° C. in a nitrogen atmosphere with triethylamine, trimethylsilylchloride and a catalytic amount of zinc chloride. After cooling to room temperature, the whole was diluted with dry ether, filtered through a Celite pad and the resulting solution was concentrated under reduced pressure at low temperature.

Distillation in vacuo of the residue gave the title compound as a colorless oil (b.p. 60° C., 0.05 mm Hg) in 60% yield.

$^1$H-NMR (CCl$_4$), internal reference CHCl$_3$ 7.25δ from TMS): τ=9.70 (s, 9H, C(2)—Si(CH$_3$)$_3$), 3.80 (d, J=3 Hz, 1H, C(4)—H), 3.25 (d, J=3 Hz, 1H, C(5)—H).

Preparation of organometallic reagent of formula VI n-Butyllithium (0.5 ml, 2.2 M solution) was added to a stirred solution of 3-bromo-2-trimethylsilyloxyfuran [VIII; R=—Si(CH$_3$)$_3$] (294 mg) in absolute ether (3 ml.) at −78° C. and stirred for 1 hour. The ether solution now contains the organometallic reagent of formula VI.

EXAMPLE II

Preparation of 4-bromo-2-trimethylsilyloxyfuran (formula VII above) [R=Si(CH$_3$)$_3$]

The title compound was prepared from the known β-bromocrotonolactone (m.p. 77° C., Beil. 17, Erg. III/IV 4296) using the same procedure adopted to prepare its 3-bromo-isomer.

The 4-bromo-2-trimethylsilyloxyfuran was obtained in 80% yield as a colorless oil after distillation in vacuo (b.p. 60° C., 0.05 mm Hg.).

$^1$H-NMR (CCl$_4$, internal reference CHCl$_3$ 7.25 from TMS): τ=9.74 (s, 9H, C(2)—Si(CH$_3$)$_3$-, 4.84 (d, J=1.5 Hz, 1H, C(3)—H), 3.20 (d,J=1.5 Hz, 1H, C(5)—H).

Preparation of organometallic reagent of formula V n-butyllithium (0.25 ml., 2.4 M solution) was added to a stirred solution of 4-bromo-2-trimethylsilyloxyfuran [VII; R=—Si(CH$_3$)$_3$] (254 mg.) in absolute ether (2.5 ml.) at −78° C. and stirred for 30 minutes. The ether solution now contains the organometallic reagent of formula V.

EXAMPLE III

Preparation of compound (2) of the accompanying FIGURE

The mixture of the α,β-unsaturated ketone (1) (3.78 g) in acetone (40 ml) and 3 N aqueous hydrochloric acid solution (10 ml) was refluxed for 1 hour. The solution was cooled, the crude crystalline β,γ-unsaturated ketone was filtered, washed with acetone and recrystallized from chloroform-ethyl ether to give pure β,γ-unsaturated ketone (2) (2.7 g.). The filtrate was neutralized with saturated NaHCO$_3$, followed by evaporation of the solvent. The residue was diluted with water, extracted with chloroform, dried over MgSO$_4$ and evaporated to dryness. The combined residue and mother liquor were purified by column chromatography on silica gel to yield the pure β,γ-unsaturated ketone (2) 860 mg). The total yield of pure compound (2) was 90% .m.p. 180°-181° C. (chloroforme—thyl ether).

Mass spectrum: Calc. for C$_{26}$H$_{34}$O$_2$: 378; Found: 378.
Elemental analysis:
Calc. for C$_{26}$H$_{34}$O$_2$: C, 82.49; H, 9.05%; Found: C, 82.49; H, 9.13%.
IR (CHCl$_3$): 1740 cm (>=O)
$^1$H-NMR (CDCl$_3$): τ=2.66 (s, 5H, benzyl aromatic), 4.50 (dd, J=2 Hz, 1H, 15—H), 5.50 (s, 2H, benzylic), 6.28 (broad s, 1H, 3—H), 7.06 (dd, J=2 Hz, 16—H), 8.88 (s, 3H, 19-methyl), 8.98 (s, 3H, 18-methyl).

Preparation of compound (3) of the accompanying FIGURE

A mixture of the β,γ-unsaturated ketone (2) (3.56 g) in benzene (100 ml), ethanol (200 ml), 0.1 N aqueous potassium hydroxide (5 ml) and 10% Pd/CaCO$_3$ (712 mg) was hydrogenated for 8 hours followed by filtration, neutralization with dilute HCl and evaporation to give the saturated ketone (3) (3.25 g, 90%) which crystallized from chloroformethyl ether, m.p. 119°-120.5° C. (chloroformethyl ether).

Mass spectrum: Calc. for C$_{26}$H$_{36}$O$_2$: 380; Found: 380.
Elemental analysis:
Calc. for C$_{26}$H$_{36}$O$_2$: C, 82.06; H, 9.54%; Found: C, 82.06; H, 9.54%.
IR (KBr): 1740 cm$^{-1}$ (>=O)
$^1$H-NMR (CDCl$_3$): τ=2.62 (s, 5H, benzyl aromatic), 5.48 (s, 2H, benzylic), 6.26 (broad s, 1H, 3—H), 8.92 (s, 3H, 19-methyl), 9.05 (s, 3H, 18-methyl).

EXAMPLE IV

Preparation of compound (4b) of the accompanying FIGURE n-Butyllithium (0.5 ml, 2.2 M solution) was added to a stirred solution of 3-bromo-2-trimethylsilyloxyfuran VIII [R=Si(CH$_3$)$_3$] (294 mg) in absolute ether (3 ml) at −78° C. and stirred for 1 hour. After which the ketone (3) (190 mg) in a mixture of benzene (1.5 ml) and absolute ether (3 ml) was added dropwise and the solution was stirred for 1 hour at the same temperature. The reaction mixture was diluted with benzene and ether, washed with water, dried over anhydrous MgSO$_4$ and evaporated to dryness. The crude material was purified by preparative thin layer chromatography (TLC) to give compound (4b) in a yield of 89%, m.p. 197°-198° C. (chloroform-ethyl ether).

Elemental analysis: Calc. for C$_{30}$H$_{40}$O$_4$: C, 77.55; H, 9.68%; Found: C, 77.39; H, 8.78%.

Mass Spectrum: Calc. for $C_{30}H_{40}O_4$: 464 Found: 464.
IR ($CHCl_3$): 3500 (OH), 1740 cm$^{-1}$ ($>$=O)

$^1$H-NMR ($CDCl_3$): $\tau$=2.66 (s, 5H, benzyl aromatic), 2.90 (t, J=1 Hz, 1H, 22—H), 5.18 (d, J=2 Hz, 23—H), 5.50 (s, 2H benzylic), 6.26 (broad s, 1H, 3—H), 9.06 (s, 3H, 19-methyl), 9.18 (s, 3H, 18-methyl).

Preparation of compound (6) of the accompanying FIGURE

Compound (4b) (1.2 g) in a mixture of benzene (60 ml) and ethanol (120 ml) was hydrogenated over 10% Pd/C (240 mg) at room temperature for 3 hours followed by filtration and evaporation to give (6) (903 mg, 93%) which was crystallized from chloroform-ethyl ether, m.p. 228° C.

Mass spectrum: Calc. for $C_{23}H_{34}O_4$: 374; Found: 374.
Elemental analysis: Calc. for $C_{23}H_{34}O_4$: C, 73.76; H, 9.15%; Found: C, 73.26; H, 9.26%. IR (KBr): 3500 (—OH), 1737 cm$^{-1}$ ($>$=O)

$^1$H-NMR ($CDCl_3$): $\tau$=2.92 (t, J=2 Hz, 1H, 22—H), 5.18 (d, J=2 Hz, 2H, 23—H), 5.56 (s, 1H, 17—OH), 5.88 (broad s, 1H, 3—H), 9.06 (s, 3H, 19-methyl), 9.18 (s, 3H, 18-methyl).

Preparation of compound (8) of the accompanying FIGURE

Compound (6) (56 mg), 1.2-dichloroethane (5 ml), dry silver oxide (139 mg) and anhydrous $MgSO_4$ (280 mg) were stirred for 1 hour at room temperature, then tetra-O-acetyl-α-D-glucopyranosyl bromide (185 mg) in 1,2-dichloroethane (1 ml) added dropwise, and stirring continued another 24 hours. The mixture was filtered and evaporated to a yellow oil. The crude compound was purified by preparative TLC to give (8) (92 mg, 87%) which was crystallized from chloroform-ethyl ether, m.p. 216°-224° C.

Elemental analysis: Calc. $C_{37}H_{52}O_{13}$: C, 63.05; H, 7.44%; Found: C, 63.02; H, 7.53%.

IR ($CHCl_3$): 3425 (—OH), 1750 cm$^{-1}$ ($>$=O),acetate)

$^1$H-NMR ($CDCl_3$): $\tau$=2.90 (t, J=2 Hz, 1H, 22—H), 4.90 (m, 3H, 2', 3', 4'—H), 5.16 (d, J=2 Hz, 2H, 23—H), 5.44 (d, J=6.5 Hz, 1H, 1'—H), 5.81 (m, 2H, 6'—H), 5.96 (broad s, 1H, 5'—H), 6.36 (broad s, 1H, 3—H), 7.91 (s,3H, 6'—C OAc), 7.96 (s, 9H, 2', 3', 4'—C OAc), 9.10 (s, 3H, 19—methyl), 9.17 (s, 3H, 18-methyl).

Preparation of compound (9)

A solution of (8) (1.87 g) in methylene chloride (6 ml), methanol (30 ml) and methanol saturated with anhydrous ammonia (60 ml) was allowed to stand overnight (15 hours) in the refrigeration (+4° C.). The clear solution was evaporated to a colorless glass which was crystallized from methanol-ethyl ether to give (9) (1.12 g, 79%), m.p. 220°-228° C. Compound (9), 17α-hydroxy-14 desoxy actodigine glucoside, is an artificial synthetic analogue of natural cardiotonic glycosides with a modified lactone attachment.

Mass spectrum: Calc. for $C_{29}H_{44}O_9$: 536; Found: 536.
IR (KBr): 3480, 3310 (—OH), 1725 cm$^{-1}$ ($>$=O)
$^1$H-NMR (DMSO-$d_6$=$CDCl_3$): $\tau$=2.83 (t, J=2 Hz, 1H, 22—H), 5.13 (d, J=2 Hz, 2H, 23—H), 9.06 (s, 3H, 19-methyl), 9.18 (s, 3H, 18-methyl).

Preparation of compound (5b) of the accompanying FIGURE

N-Butyllithium (0.25 ml, 2.4 M solution) was added to a stirred solution of 4-bromo-2-trimethylsilyloxyfuran VII [R=Si(CH$_3$)$_3$] (254 mg) in absolute ether (2.5 ml) at −78° C. and stirred for 30 minutes. After which the ketone (3) (137 mg) in a mixture of benzene (1 ml) and ether (2 ml) was added dropwise and the solution was stirred for 1.5 hours at the same temperature. The reaction mixture was diluted with benzene and ether, washed with water, dried over anhydrous $MgSO_4$ and evaporated to dryness. The crude compound was purified by preparative TLC to give (5 b) in a yield of 94%, m.p. 175°-177° C. (chloroform-ethyl ether).

Mass spectrum: Calc. for $C_{30}H_{40}O_4$: 464; Found: 464.
Elemental analysis: Calc. for $C_{30}H_{40}O_4$: C, 77.55; H, 8.68%; Found: C, 77.25; H, 8.75%.

IR ($CHCl_3$): 3600, 3450 (—OH), 1785, 1745 cm$^{-1}$ ($>$=O)

$^1$H-NMR ($CDCl_3$): $\tau$=2.69 (s, 5H, benzyl aromatic), 4.23 (t, J=1 Hz, 1H, 22—H), 5.08 (t, J=2 Hz, 2H, 21—H), 6.28 (broad s, 1H, 3—H), 9.06 (s, 3H, 19-methyl), 9.16 (s, 3H, 18-methyl).

Preparation of compound (7) of the accompanying FIGURE

Compound (5b) (3.10 g) in a mixture of benzene (120 ml) and ethanol (240 mg) was hydrogenated over 10% Pd/C (620 mg) at room temperature for 3 hours followed by filtration and evaporation to give (7) (2.24 g, 90%) which was crystallized from chloroformethyl ether, m.p. 209°-211° C.

Mass spectrum: Calc. for $C_{23}H_{34}O_4$: 374; Found: 374.
Elemental analysis:
Calc. for $C_{23}H_{34}O_4$: C, 73.76; H, 9.15%; Found: C, 73.20; H, 9.19%.

IR (KBr): 3474, 3375 (—OH), 1800,1750 cm$^{-1}$ ($>$=O)

$^1$H-NMR ($CDCl_3$): $\tau$=4.20 (t, J=2 Hz, 1H, 22—H), 5.06 (t, J=2 Hz, 2H, 21—H), 5.86 (broad s, 1H, 3—H), 9.06 (s, 3H, 19-methyl), 9.16 (s, 3H, 18-methyl).

Preparation of compound (10) of the accompanying FIGURE

Compound (7) (56 mg), 1,2-dichloroethane (5 ml) dry silver oxide (139 mg) and anhydrous $MgSO_4$ (280 mg) were stirred 1 hour at room temperature, then tetra-O-acetyl-α-D-glucopyranosyl bromide (185 mg) in 1,2-dichloroethane (1 ml) added dropwise, and stirring continued another 24 hours. The mixture was filtered and evaporated to a yellow oil. The crude compound was purified by preparative TLC to give (10) (85 mg, 81%) which was crystallized from chloroform-ethyl ether, m.p. 223°-225° C.

Elemental analysis: Calc. for $C_{37}H_{52}O_{13}$: C,63.05; H,7.44%; Found: C,62.93; H,7.42%.

IR (KBr): 3620 (—OH), 1760 cm$^{-1}$ ($>$=O), acetate)
$^1$H-NMR ($CDCl_3$): $\tau$=4.16 (t, J=2 Hz, 1H, 22—H), 4.91 (m, 3H, 2', 3', 4'—H), 5.06 (d, J=2 Hz, 2H, 21—H), 5.44 (d, J—6.5 Hz, 1H, 1'—H), 5.81 (m, 2H, 6'—H), 5.96 (broad s, 1H, 5'—H), 6.36 (broad s, 1H, 3—H), 7.91 (s, 3H, 6'—C OAc), 7.96 (s, 9H, 2', 3', 4'—C OAc), 9.10 (s, 3H, 19-methyl), 9.17 (s, 3H, 18-methyl).

Preparation of compound (11) of the accompanying FIGURE

A solution of (10) (2 g) in methylene chloride (12 ml), methanol (30 ml) and methanol saturated with anhydrous ammonia (60 ml) was allowed to stand overnight (15 hours) in the refrigerator (+4° C.). The clear solution was evaporated to a colorless glass which was crystallized from methanol-ethyl ether to give (11) (1.2 g, 80%), m.p. 239°–244° C. Compound (11), 17α-hydroxy 14-desoxy digitoxigenine glucoside, is an artificial synthetic analogue of natural cardiotonic glycosides with a normal lactone attachment.

Mass spectrum: Calc. for $C_{29}H_{44}O_9$: 536; Found: 536.

IR (KBr): 3425 (—OH), 1755 cm$^{-1}$ (>=O)

$^1$H-NMR (DMSO-d$_6$+CDCl$_3$): τ=4.26 (t, J=2 Hz, 1H, 22—H), 5.06 (d, J=2 Hz, 2H, 21—H), 9.10 (s, 3H, 19-methyl), 9.20 (s, 3H, 19-methyl).

In accordance with the above, any kind of digitoxigenine or actodigine derivative with modified substitutions can be prepared in the same manner. Specifically, the 12β-hydroxy and 11α-hydroxy derivatives can be prepared.

BEST MODE CONTEMPLATED

The best mode contemplated for carrying out this invention has been set forth in the description above, for example, by way of setting forth preferred structural arrangements, materials, used, compositions and operating conditions, including but not limited to preferred ranges and values of amounts, temperatures, pressures, and other unobvious variable materials to successfully practicing (including making and using) the invention in the best way contemplated at the time of executing this patent application.

It is understood that the foregoing detailed description is given merely by way of illustration and that many modifications may be made therein without departing from the spirit or scope of the present invention.

What I claim is:

1. A method for synthesizing a cardenolide or an isocardenolide which comprises the steps of:
   (a) subjecting an α,β-unsaturated steroidal 17-ketone to an acid catalyzed double bond shift followed by hydrogenation to produce a (C/D cisoid) ketone;
   (b) treating said ketone with an organo-metallic reagent selected from the group consisting of

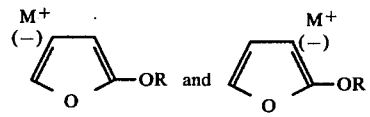

where R is a readily removable blocking group and M$^+$ is a metal ion to yield a labile tertiary alcohol; and
   (c) acidifying said alcohol to produce said cardenolide or isocardenolide.

2. The method of claim 1 which additionally comprises the steps of:
   (d) hydrogenolysis of said cardenolide or isocardenolide to produce the corresponding alcohol;
   (e) converting said alcohol to the corresponding glucoside acetate; and
   (f) converting said glucoside acetate to the corresponding β-glucoside.

3. The method of claim 1 wherein R is selected from the group consisting of alkyl, trialkylsilyl, alkoxyalkylene, aralkyl, aloxy aralkyl, and tertiary alkyl and wherein said alkyl, alkoxy or alkylene group has from one to four carbon atoms.

4. The method of claim 1 wherein R is selected from the group consisting of trimethylsilyl, methyl, methoxy methylene, benzyl, p-methoxybenzyl and tertiary butyl.

5. The method of claim 1 wherein M$^+$ is selected from the group consisting of Li$^+$, Na$^+$, K$^+$ and Mg$^{++}$(halogen)$^-$.

6. The method of claim 1 wherein M$^+$ is Li$^+$.

* * * * *